(12) United States Patent
Eden et al.

(10) Patent No.: US 6,395,537 B1
(45) Date of Patent: May 28, 2002

(54) DOUBLE CONTAINER DEVICE AND METHOD FOR DETECTING AND ENUMERATING MICROORGANISMS IN A SAMPLE

(76) Inventors: Ruth F. Eden; Gideon Eden, both of 2765 Ember Way, Ann Arbor, MI (US) 48104

( * ) Notice: Subject to any disclaimer, the term of this patent is extended or adjusted under 35 U.S.C. 154(b) by 0 days.

(21) Appl. No.: 09/922,444

(22) Filed: Aug. 4, 2001

(51) Int. Cl.⁷ ............................................. C12M 1/34
(52) U.S. Cl. .................. 435/287.1; 435/287.5; 435/287.7; 435/288.1; 435/288.7
(58) Field of Search ................ 435/287.1, 287.7, 435/288.1, 288.2, 288.7, 808, 287.5

(56) References Cited

U.S. PATENT DOCUMENTS

| | | | | |
|---|---|---|---|---|
| 4,728,607 A | * | 3/1988 | Dorn et al. ................. | 359/398 |
| 4,868,110 A | * | 9/1989 | DesRosier et al. .......... | 422/102 |
| 4,945,060 A | * | 7/1990 | Turner et al. ............. | 435/288.7 |
| 5,094,955 A | * | 3/1992 | Calandra et al. ............... | 422/52 |
| 5,164,796 A | * | 11/1992 | Di Guiseppi et al. ........ | 356/445 |
| 5,217,876 A | * | 6/1993 | Turner et al. .................. | 422/52 |
| 5,366,873 A | * | 11/1994 | Eden et al. ............... | 435/288.2 |
| 5,672,484 A | * | 9/1997 | Eden et al. ............... | 435/287.7 |
| 5,976,827 A | * | 11/1999 | Jeffrey et al. ............. | 435/287.7 |
| 6,197,577 B1 | * | 3/2001 | Jeffrey et al. ............. | 435/287.8 |

* cited by examiner

*Primary Examiner*—David A. Redding
(74) *Attorney, Agent, or Firm*—James M. Deimen

(57) ABSTRACT

A device for detecting and enumerating microorganisms in a sample substance employs an external container and an internal container inserted into the headspace of the external container. The sample is mixed with liquid growth media in the internal container. Gases generated from the metabolic activity of the microorganisms during incubation expand to the headspace of the sealed external container and interact with an indicator located at a transparent section of the external container. Changes of the indicator are read by an external real time photometer that generates time patterns for analysis. These patterns indicate the presence or absence of microorganisms and assess the level of contamination in the original sample.

14 Claims, 3 Drawing Sheets

DOUBLE CONTAINER DEVICE AND METHOD FOR DETECTING AND ENUMERATING MICROORGANISMS IN A SAMPLE

FIELD OF THE INVENTION

The present invention relates to a device for detecting microbial growth and enumerating the microorganisms present in a sample, and means to accelerate their growth rate.

BACKGROUND OF THE INVENTION

It is necessary to test various industrial samples, such as food, pharmaceuticals, cosmetics and water for microbial contamination One area of microbiological testing involves the estimation of total number of bacteria, yeast and molds as well as contamination of specific groups of organisms in the sample. One widely used method is known as the "Standard Plate Count" method and involves culturing a diluted sample in an agar growth medium The plates containing the sample and the growth medium are incubated (e.g., 32° C.–40° C.) for 24 hours to 5 days depending upon the assay. After incubation, colonies of microorganisms that have been grown upon the agar surface are counted. Optical methods based upon color change have been successfully used to classify microorganisms in clinical samples. Turner describes in U.S. Pat. No. 4,945,060 noninvasive means for detecting the presence of microorganisms in clinical specimens with an optical sensor located at the bottom of a culture bottle. The sensor comprises a solid composition or a membrane with an indicator substance immobilized on or within it. The metabolic products of the organisms growing in the liquid media diffusse to the solid sensor and change the color of the indicator. Similar devices are disclosed in U.S. Pat. Nos. 5,094,955, 5,164,796, 5,217,876 and PCT WO 96/39533. All of these devices comprise sensors made of a semi-permeable layer such as a membrane or cured polymer, The problem with these devices is that the diffusion rate of the metabolic products is not uniform and can vary from one culture bottle to another. Consequently these devices have been used to detect only the presence of microorganisms, and not for enumeration tests.

Another device, disclosed by Eden in U.S. Pat. No. 5,366,873, comprises a container with growth media and indicator substance disposed in the media for undergoing transformation in the presence of organisms growth. Since the indicator substance is in the media, changes in color due to microbial growth are detected rapidly and consistently in the indicator. A layer of semi-fluid substance, such as agar, containing the same chemical compounds present in the liquid media, is in chemical equilibrium with the media and consequently reflects the changes occurring in the media while preventing the food particles and microorganisms from masking these changes. This device can be used for enumeration of organisms in a sample based upon the consistency of the patterns obtained when using a photometer recording the optical changes of the indicator on-line. The present invention introduces new and different means to change the properties of an optical indicator. The changes result from the generation of gases from metabolic activity of microorganisms.

SUMMARY OF THE INVENTION

One of the advantages of the present invention is the capability to detect organisms (e.g. molds) which the devices recited in the prior art cannot detect. Another advantage of the invention is its capability to enhance growth of aerobic microorganisms by employing a highly porous material or an agar slant which increases the surface area for microbial exposure to oxygenated growth media. The concept of the porous material has been introduced in U.S. Pat. No. 5,672,484 and the agar slant is a well-known technology in microbiology. These enhancements are now combined in the new invention in order to optimize the optically based technology disclosed.

In accordance with the present invention an external container with at least one transparent portion contains an indicator capable of changing color due to gases produced by microbial metabolism. An internal container is placed inside the external container and occupies a portion of the headspace of the external container. The internal container contains appropriate growth media to promote microbial growth and the sample to be tested. The uncovered internal container is placed inside the external container and the external container is capped. The assembly is than incubated at an appropriate temperature. Due to microbial growth, gases such as $CO_2$ are produced. The generated gases are released from the internal container to the headspace of the external container and a chemical reaction occurs between the gases and the chemicals in the transparent portion of the external container, causing the indicator to change color. This color change is monitored either visually or optically by an external photometer.

BRIEF DESCRIPTION OF THE DRAWING

Other advantages of the present invention will be readily appreciated as the same becomes better understood by reference to the following detailed description when considered in connection with the accompanying drawings wherein.

DETAILED DESCRIPTION OF THE INVENTION

Figure 1:
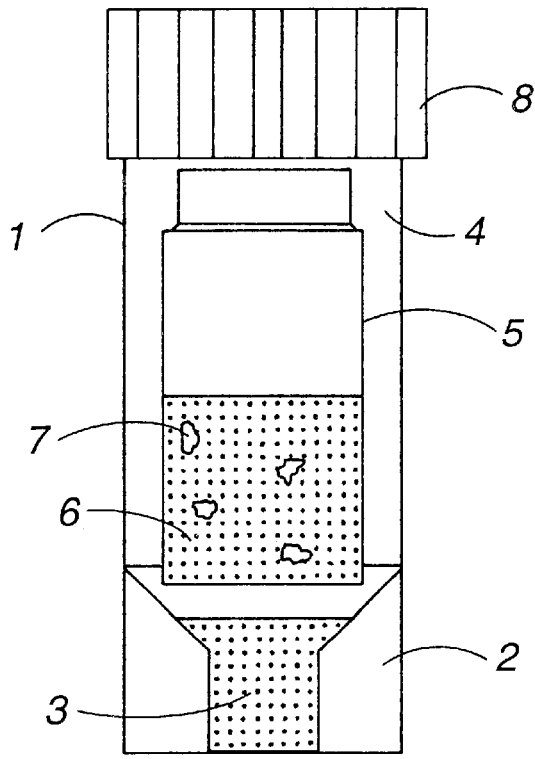
FIG. 1: Illustrates the external and internal containers of the preferred embodiment of the invention.

FIG. 1 illustrates the preferred embodiment of the invention. An external container 1 has a cap 8 that can airtight seal the headspace 4 of the container. The external container 1 can be made of any material such as plastic or glass. At least one portion of the external container is transparent to electromagnetic energy. The transparent section 2 contains optical indicator 3 that can be visually inspected or monitored by an external electronic detector. The indicator 3 is capable of transforming when exposed to gases generated by metabolic activity of microorganisms. In its simplest form a suitable $CO_2$ absorbent containing a pH indicator is used. It is capable of changing color as it absorbs $CO_2$ generated by the microorganisms. The absorbtion of $CO_2$ by KOH undergoes the following chemical reaction:

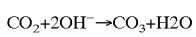

This reaction results in a pH reduction, which is detected by the liquid dye, such as Thymolphthalein, mixed with the KOH base. In another embodiment these chemical compounds are part of a semi-liquid matrix such as agar. The indicator itself can be a dye, fluorescent or luminescent compound operating in the visible or ultraviolet spectrum range.

An internal container 5 is placed inside the external container 1 to occupy the headspace 4 of the external container. The internal container 5 contains the sample substance 7 to be tested and appropriate growth media 6 to promote efficient microbial growth and consequent generation of gases due to microbial metabolism. After insertion of the internal container 5 into the external container 1, the latter is sealed with the cap 8 and the assembly is placed in an incubator which is set to an optimized temperature for microbial growth.

The organisms grow in the liquid media in the internal container 5 and generate at least one gas from their metabolic activity. Placing the device in a shaker during incubation can further enhance gas generation. The shaker can enhance oxygenation of the media 6 from air present in the headspace 4 and can accelerate the release of the bacterial generated gases from the media 6 to the headspace 4. The most common gas generated by microorganisms is carbon dioxide but other gases can also be generated. Since the internal container 5 is placed unsealed into the external container 1, the generated gas is released from the internal container to fill the headspace of the external container. Therefore the generated gas travels to the surface of the indicator 3 and interacts with its chemical compounds. For example, generated carbon dioxide interacts with the KOH compound to lower its pH. The Thymolphthalein dye changes from blue at pH=9 (or higher) to colorless at lower pH values. This color change can be observed via the transparent section 2 for the determination of the presence of microorganisms. Alternatively, an external photometer can record the color change as a function of time and store the pattern in memory for further analysis, thereby allowing the determination of the number of the organisms in the original sample.

Figure 2A:
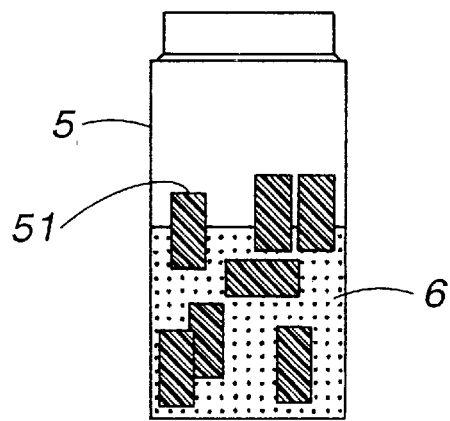
FIG. 2a: Illustrates the porous material to increase microbial growth.
Figure 2B:
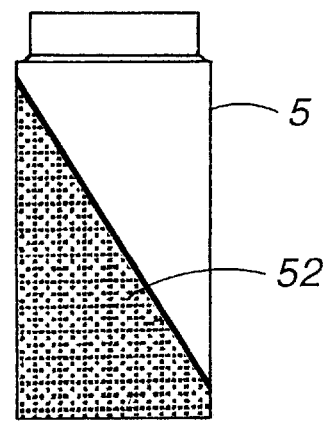
FIG. 2b: Illustrates the agar slant to increase microbial growth.

FIG. 2 demonstrates two enhancements to the preferred embodiment. In FIG. 1 the internal container 5 contains the sample and growth media. In FIG. 2a the internal container 5 also includes porous material inserts 51, fully or partially immersed in the liquid media 6. The inserts increase surface area and support microorganisms suspended with or on the inserts to increase microbial exposure to oxygenated media and thereby enhance microbial metabolism. The porous material inserts 51 can be made of synthetic sponge materials, cotton, fiberglass, Porex™, paper, or any other porous plastic. In FIG. 2b the liquid media 6 in the internal container 5 is replaced by an agar slant 52 which contains the media compounds embedded in gelatin matrix. The sample is placed along the surface of the slant that has a relatively large surface area and thereby enhance the microbial growth.

EXAMPLES

Example 1

The internal containers were filled with 3.5 ml of Yeast Peptone Dextrose Broth (Yeast extract 10.0 gm/l, Peptone 20.0 gm/l, Dextrose 20.0 gm/l, pH: 5.6±0.2) or Yeast Peptone Agar containing additionally 1.5% agar. Fruit molds were inoculated into the inner container at equal concentrations. The inoculated inner containers were fitted into the external container, incubated at 30° C. and monitored every 6 minutes by an optical system For each mold, three inner containers were tested: (I) containing sponge inserts in the broth as described in FIG. 2a; (II) containing the agar medium in a slant format as described in FIG. 2b; (III) inner container with broth only.

Figure 3:
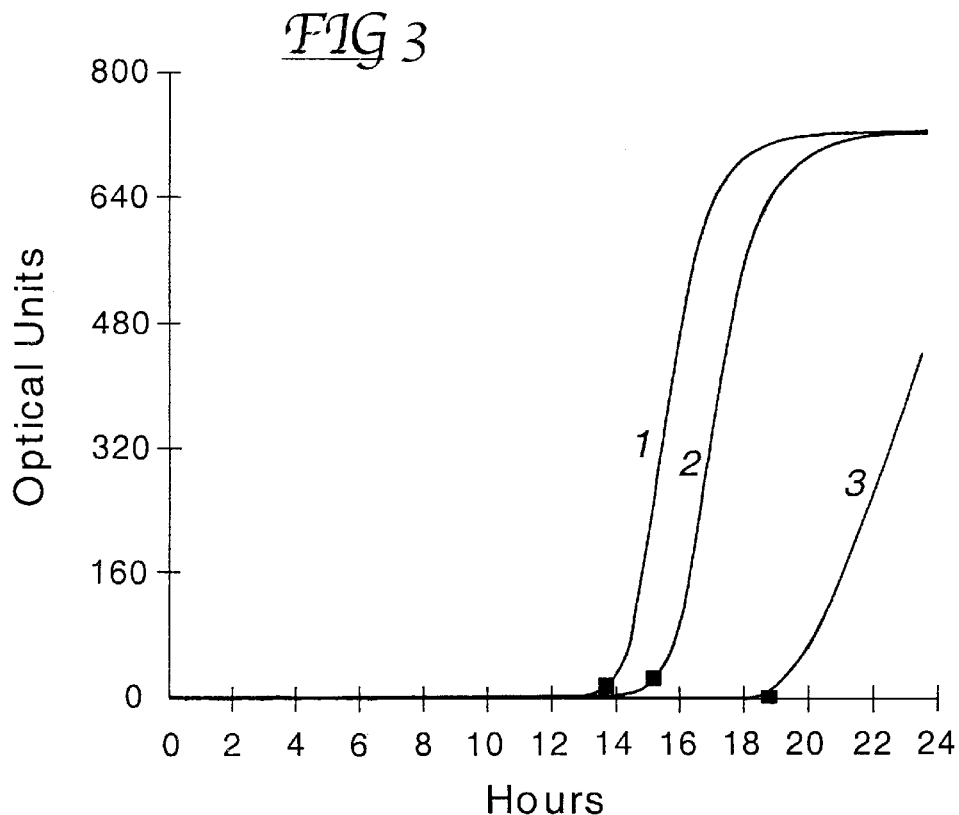
FIG. 3: Shows a time pattern of color change of the detector during the growth of mold.

The two embodiments illustrated in FIG. 2 were successfully used to detect molds that could not otherwise be detected in the devices recited in the prior art. FIG. 3 shows a typical time pattern generated by the device illustrated in FIG. 1 using an external photometer reading the color changes of the indicator. The occurrence in time of the deflection point is defined as "detection time". In FIG. 3 the result of the same concentration of a fruit mold with three different internal containers is shows Curve 1 was obtained with the inner container described in FIG. 2a, curve 2 was obtained with inner container described in FIG. 2b, while curve 3 was obtained with an inner container containing only broth. It can be seen that the detection time with the inner container with the sponge inserts (curve 1) was 5.5 hours (29%) faster than in the broth (curve 3). The slant inner container (curve 2) had a detection time that was 4.5 hour (24%) faster than the broth alone. Similar results were obtained with other molds. These results indicate that the inner containers described in FIG. 2 contribute significantly to the decrease in the time necessary to detect molds.

Example 2

The internal container was filled with 3.5 ml of Brain Heart Infusion (Difco Laboratories, Inc.), containing (37.0 gm/l) with L-Histidine (Sigma-Aldrich Chemicals) 2.5 gm/l. A culture of the bacteria *Pseudomonas flourescens* ATCC 13525 was decimally diluted six times. Each dilution was inoculated into a different inner container. The inoculated inner containers were placed in the external containers, incubated at 35° C. and monitored every 6 minutes by an optical detector.

Figure 4:
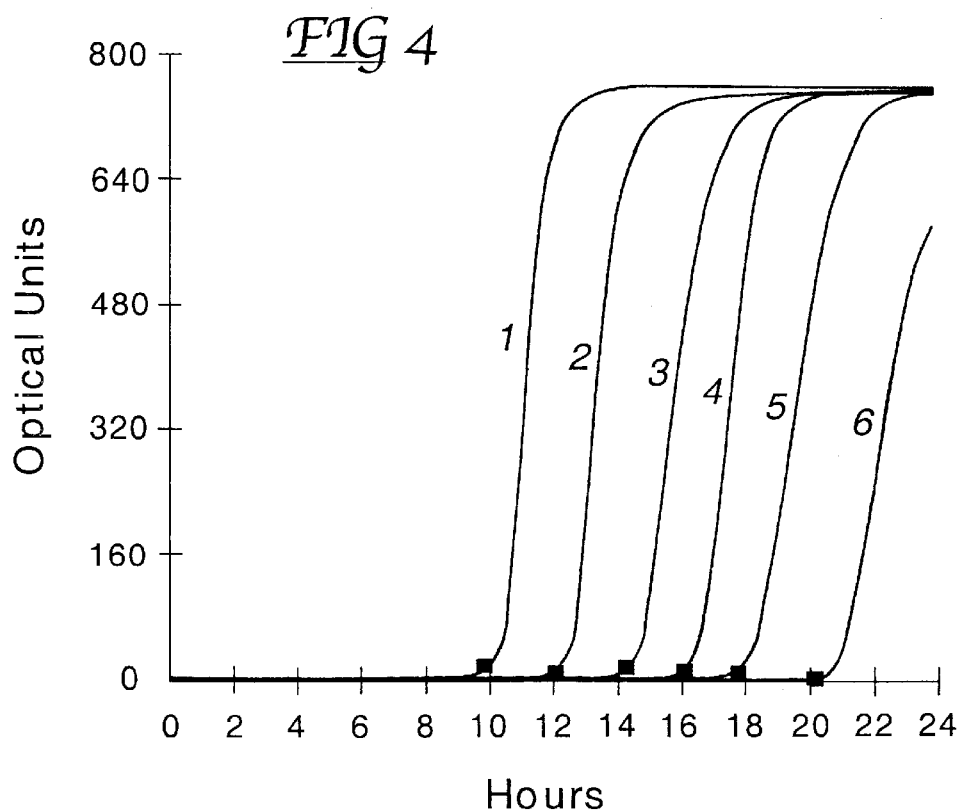
FIG. 4: Shows a time pattern of color change of the detector during the growth of *Pseudomonas flourescens* ATCC 13525.
Figure 5:
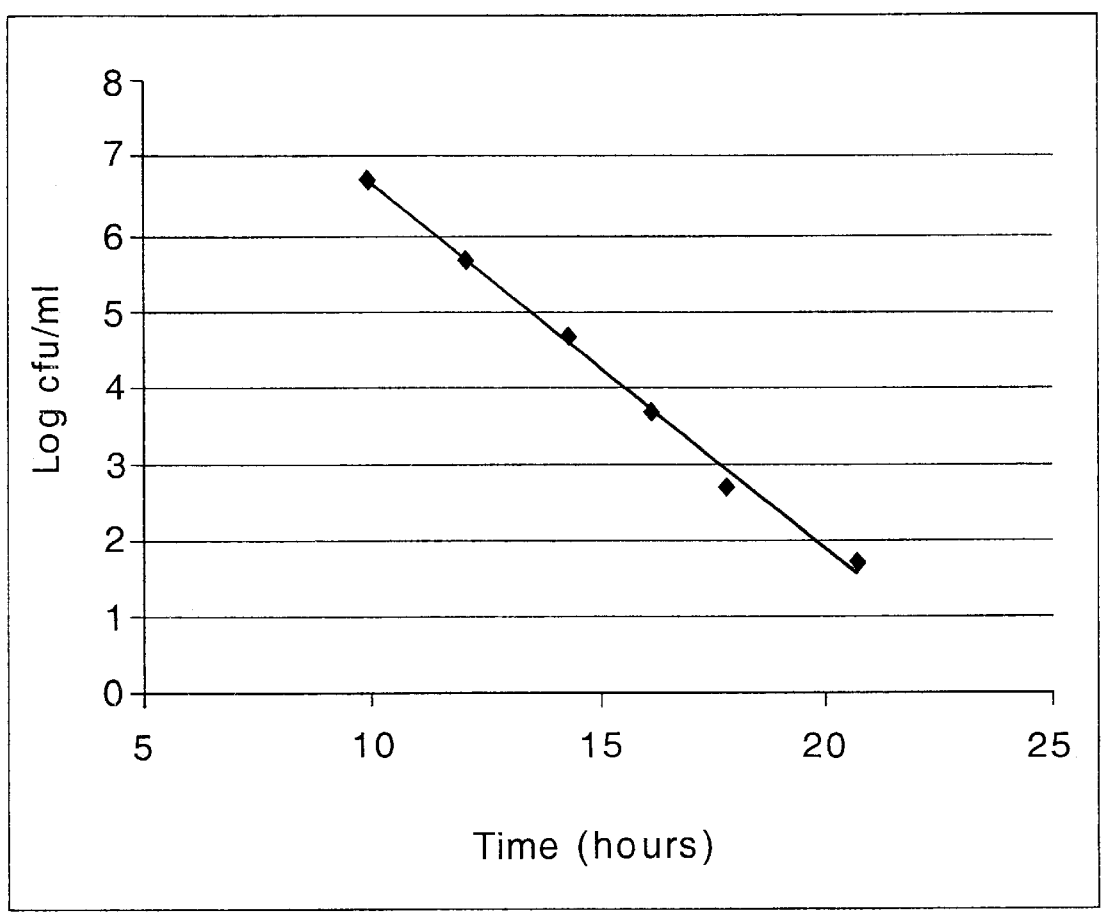
FIG. 5: Shows a typical calibration curve, relating counts by the standard methodology to the time of color change.

FIG. 4 shows the six curves obtained. Curve 1 was obtained from the sample containing the most concentrated level of bacteria ($5*10^6$ bacteria/container), curve 2 contained $5*10^5$ bacteria/container, curve 3 contained $5*10^4$ bacteria/container, curve 4 contained $5*10^3$ bacteria/container, curve 5 contained $5*10^2$ bacteria/container, and curve 6 contained $5*10^1$ organisms/container. It can be seen that there is an inverse relationship between the concentration of bacteria in the sample (Log number of bacteria per ml of sample) and the time to detection. Faster detection times indicate higher contaminated samples. FIG. 5 shows the relationship between $Log_{10}$ of numbers of bacteria per ml and times to detection. A calibration curve such as shown in FIG. 5 can be used to transform detection times to the concentration of bacteria in the sample expressed as Colony Forming Units (CFU) in the original sample.

What is claimed is:
1. A device for detecting microbial growth from a sample substance, comprising:
   a sealable external container comprising a head-space and at least one section transparent to electromagnetic energy;
   an indicator substance, located adjacent to said transparent section, and capable of changing its optical properties in the presence of at least one gas generated during the microbial growth; and
   an internal container contained in and open to said head space of said external container, said internal container containing a mixture of the sample substance and growth media to promote growth of microorganisms in the sample substance, whereby generation of said at least one gas which thereby expands into said headspace section and interacts with said indicator substance promotes said change in the indicator substance optical properties.

2. The device of claim 1 wherein said indicator substance comprises liquid dye.

3. The device of claim 1 wherein said indicator substance comprises liquid dye embedded in semi-liquid matrix.

4. The device of claim 3 wherein said semi-liquid matrix is composed of a gelatin substance.

5. The device of claim 4 wherein said gelatin substance is agar.

6. The device of claim 1 wherein said indicator substance comprises fluorescence material in liquid form.

7. The device of claim 1 wherein said indicator substance comprises fluorescence material embedded in a semi-liquid matrix.

8. The device of claim 7 wherein said semi-liquid matrix is composed of gelatin substance.

9. The device of claim 8 wherein said gelatin substance is agar.

10. The device of claim 1 including a shaker to promote efficient and fast microbial growth.

11. The device of claim 1 wherein said at least one gas is carbon dioxide.

12. The device of claim 1 further including at least one insert made of porous material and immersed in said growth media and the sample substance in said internal container.

13. The device of claim 12 wherein said porous material is chosen from the group consisting of cotton, sponge, fiber-glass, paper and porous plastics.

14. The device of claim 1 further including an agar slant with embedded growth media in said internal container, said sample substance being smeared upon said agar slant.

* * * * *